US00PP30427P2

(12) United States Plant Patent
Bagdasarian

(10) Patent No.: US PP30,427 P2
(45) Date of Patent: Apr. 23, 2019

(54) STRAWBERRY PLANT NAMED 'EMILIA'

(50) Latin Name: *Fragaria x ananassa*
Varietal Denomination: Emilia

(71) Applicant: Jimmy Haig Bagdasarian, Santa Cruz, CA (US)

(72) Inventor: Jimmy Haig Bagdasarian, Santa Cruz, CA (US)

(73) Assignee: Lassen Canyon Nursery, Inc., Redding, CA (US)

( * ) Notice: Subject to any disclaimer, the term of this patent is extended or adjusted under 35 U.S.C. 154(b) by 0 days.

(21) Appl. No.: 15/732,843

(22) Filed: Jan. 3, 2018

(51) Int. Cl.
*A01H 5/08* (2018.01)

(52) U.S. Cl.
USPC ..... Plt./209

(58) Field of Classification Search
USPC ..... Plt./209
See application file for complete search history.

(56) References Cited

U.S. PATENT DOCUMENTS

| | | |
|---|---|---|
| PP22,472 P3 | 1/2012 | Bagdasarian |
| PP26,974 P3 | 7/2016 | Bagdasarian |
| PP27,034 P3 | 8/2016 | Bagdasarian |
| PP27,190 P3 | 9/2016 | Bagdasarian |

*Primary Examiner* — Annette H Para
(74) *Attorney, Agent, or Firm* — Phase M Legal

(57) ABSTRACT

A new and distinct variety of strawberry plant (*Fragaria* x *ananassa*) named 'Emilia' is described. This new short-day strawberry variety is characterized by large, firm fruit with an attractive light red exterior and interior color, and are long conic to wedge-shaped. The fruit have good sweet strawberry flavor. The plants of this new variety are vigorous and productive, and while this plant is short-day, it is partially remontant in cool coastal environments of California.

6 Drawing Sheets

Latin name of the genus and species of the plant claimed: Botanical classification: *Fragaria* x *ananassa.*

Variety denomination: The new strawberry variety denomination is 'Emilia.'

BACKGROUND OF THE INVENTION

Field of Invention

The present invention relates to a new and distinct strawberry variety named 'Emilia.' This new short-day variety is the result of a controlled cross in an ongoing breeding program by the inventor, Jimmy Bagdasarian, in 2009. The variety is botanically known as *Fragaria* x *ananassa*. The primary market of this variety is for fresh market sale of the fruit. 'Emilia' produces large, conical to wedge-shaped berries, which are firm, have good flavor and a light red color.

Comparison with Parent Varieties

The controlled cross which produced 'Emilia' was the result of a cross in 2009 between a strawberry variety used as a female parent designated '1D12' (an unreleased proprietary variety), and a strawberry variety used as the male pollen parent designated 'Sweet Ann,' (U.S. Plant Pat. No. 22,472).

The characteristics of the female parent '1D12' are: Short-day variety with very firm fruit which are light in color and can be a bit irregular in shape. The plant exhibits medium vigor with lighter green leaves.

The male pollen parent 'Sweet Ann' has the following characteristics: day-neutral with an open plant density and high vigor plant; leaves are medium glossy with little to no blistering; fruit are very large, conical, and sweet, with a glossy medium red color both interior and exterior, often with a white shoulder near the calyx.

'Emilia,' is a short-day plant, unlike its male parent 'Sweet Ann.' It has intermediate vigor to its parents with that more closely aligning the more vigorous 'Sweet Ann' in nature. It has firmer fruit than that of the pollen parent 'Sweet Ann,' but is not quite as firm as the fruit of the female parent '1D12.' The fruit of 'Emilia' is fairly uniform like that of 'Sweet Ann,' but also has a few misshapen fruit periodically, like '1D12.'

The cross done to create 'Emilia' was carried out in Santa Cruz, Calif., USA. Pollen taken from 'Sweet Ann' was placed onto a flower with male parts removed on '1D12' and then covered so that no other pollen could contaminate the procedure. Once the berry began to develop, the covering was removed. Ripe strawberries were then harvested, and the seed was extracted and germinated in a greenhouse in Redding, Calif., USA. The resulting seedlings were transplanted to Shastina, Calif. in 2010, grown out for an additional period, allowing them to propagate asexually through runners. Clones were then harvested and planted In breeding plots in fruiting fields in late September in: Oxnard, Calif. (Ventura County), and mid-October in Watsonville, Calif. (Monterey County). The selection of the new variety was first made in Watsonville, Calif., and given the designation '22K45' in 2011. This selection was later named 'Emilia.'

The variety was further propagated asexually by runners (stolens) in breeding plots in: Macdoel, Calif. (Siskiyou County), and Manteca, Calif. (San Joaquin County). The new variety has also been "meristemed." Small pieces of plant material of approximately 0.5 mm in diameter and consisting of the undifferentiated meristem tissue and one or two leaf primordia were removed from the buds on crowns of young daughter plants, then placed on nutrient medium, and new plants were grown from them. Planting stock from the "meristemed" plants are growing in a screenhouse located in Redding, Calif. These propagules of 'Emilia' are identical to the original plant in all distinguishing characteristics. The propagation has been monitored throughout the process, and all traits disclosed herein remain fixed and true to type through successive generations of asexual reproduction.

SUMMARY OF THE INVENTION

'Emilia' is a short-day variety exhibiting the following combination of characteristics, which have been observed repeatedly, and which distinguish this strawberry plant as a new and distinct variety:

1. The variety produces large size fruit;
2. The fruit is mostly a long conic shape, and occasionally wedge-shaped;
3. The fruit is a medium glossy, light red exterior and interior color;
4. The fruit is sweet tasting, with good flavor;
5. The variety is productive, producing a high volume of fruit;
6. The plants are vigorous and maintain an upright architecture;
7. The variety is partially remontant in cool coastal environments.

'Emilia' fruit is larger than that of its female parent '1D12, but slightly smaller than that of its paternal parent 'Sweet Ann.' The appearance of 'Emilia' is better than that of '1D12' and more similar to that of 'Sweet Ann' with the occasional crease or bump. The ripening pattern of 'Emilia' is preferred to that of 'Sweet Ann' in that it ripens more fully to the top of the berry. Under certain conditions, 'Sweet Ann' does not color all the way to the calyx, so it can be perceived as not being fully ripe. The firmness of 'Emilia' is similar to the very firm '1D12,' which is firmer than that of 'Sweet Ann.' Fruit of 'Emilia' is also a light red color, which is often preferred by shippers of fresh strawberries because darker fruit can be perceived as being overly ripe by consumers.

BRIEF DESCRIPTION OF THE DRAWINGS

The accompanying color photographs, identified as FIGS. 1 through 6, show the appearance of typical specimens of the new strawberry variety, initially designated '22K45,' and now named 'Emilia.' These figures depict the colors, as nearly true as it is reasonably possible given differences in color illustrations of this character. Accordingly, color in the photographs may differ slightly from the colors discussed in the botanical description. The photographs of the depicted plant, plant parts, and fruit of 'Emilia' were taken in October/November of 2017.

DETAILED BOTANICAL DESCRIPTION OF THE PLANT

Figure 1:
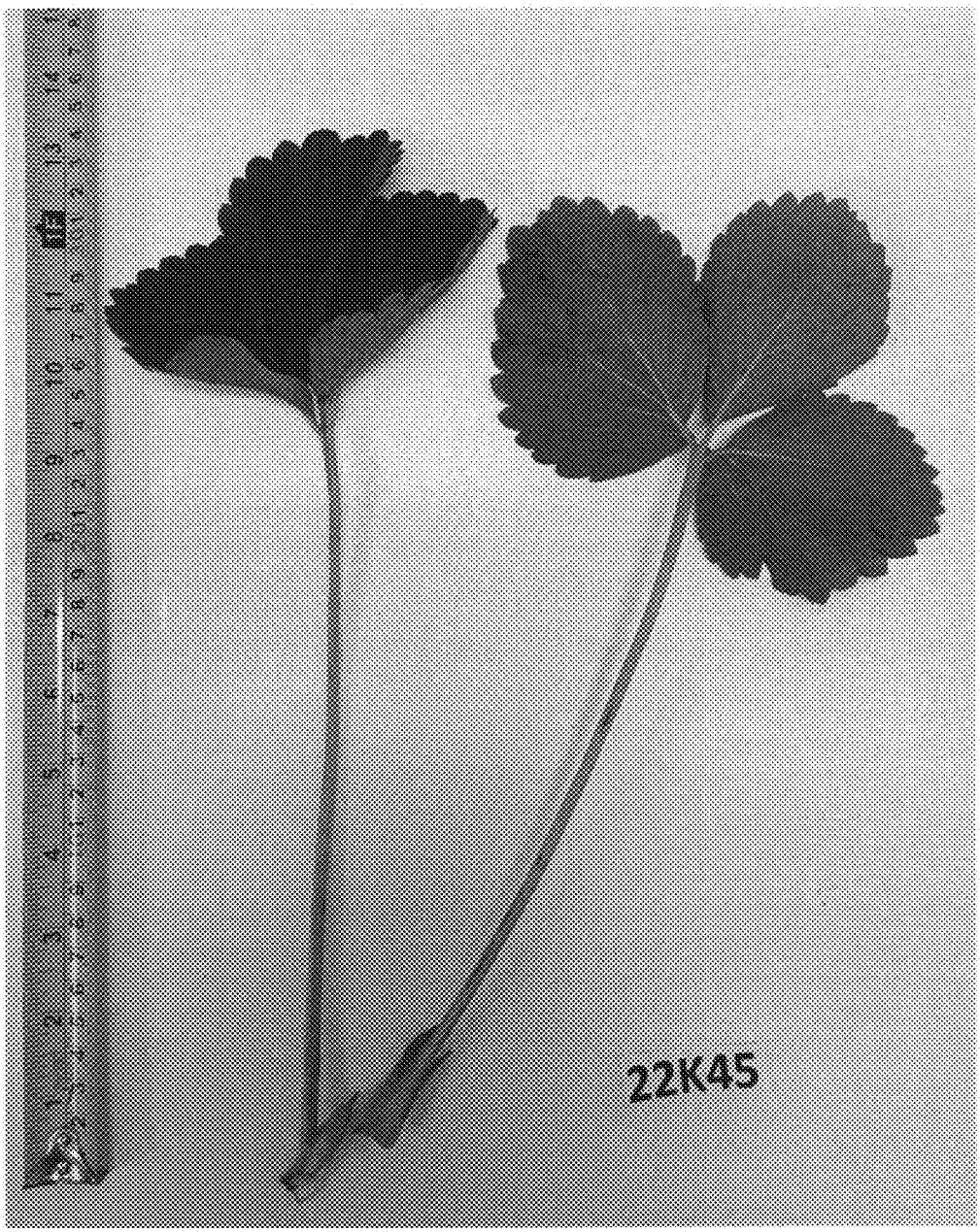
FIG. 1 shows the top and bottom of a typical leaf and petiole structure of 'Emilia;'
Figure 2:
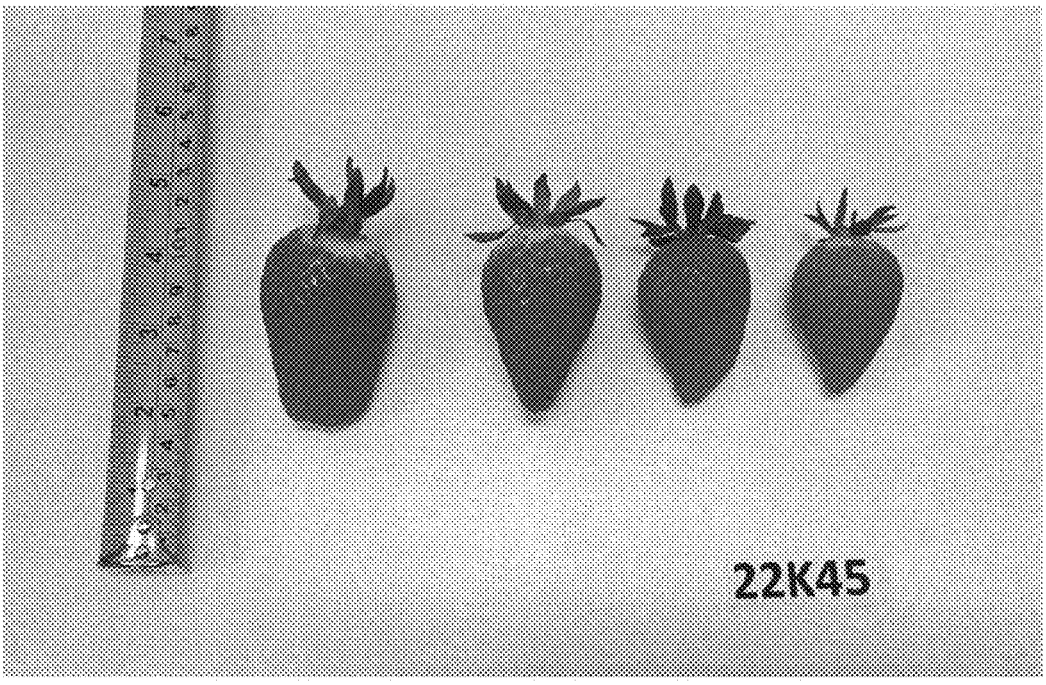
FIG. 2 shows a selection of late-season fruit.
Figure 3:
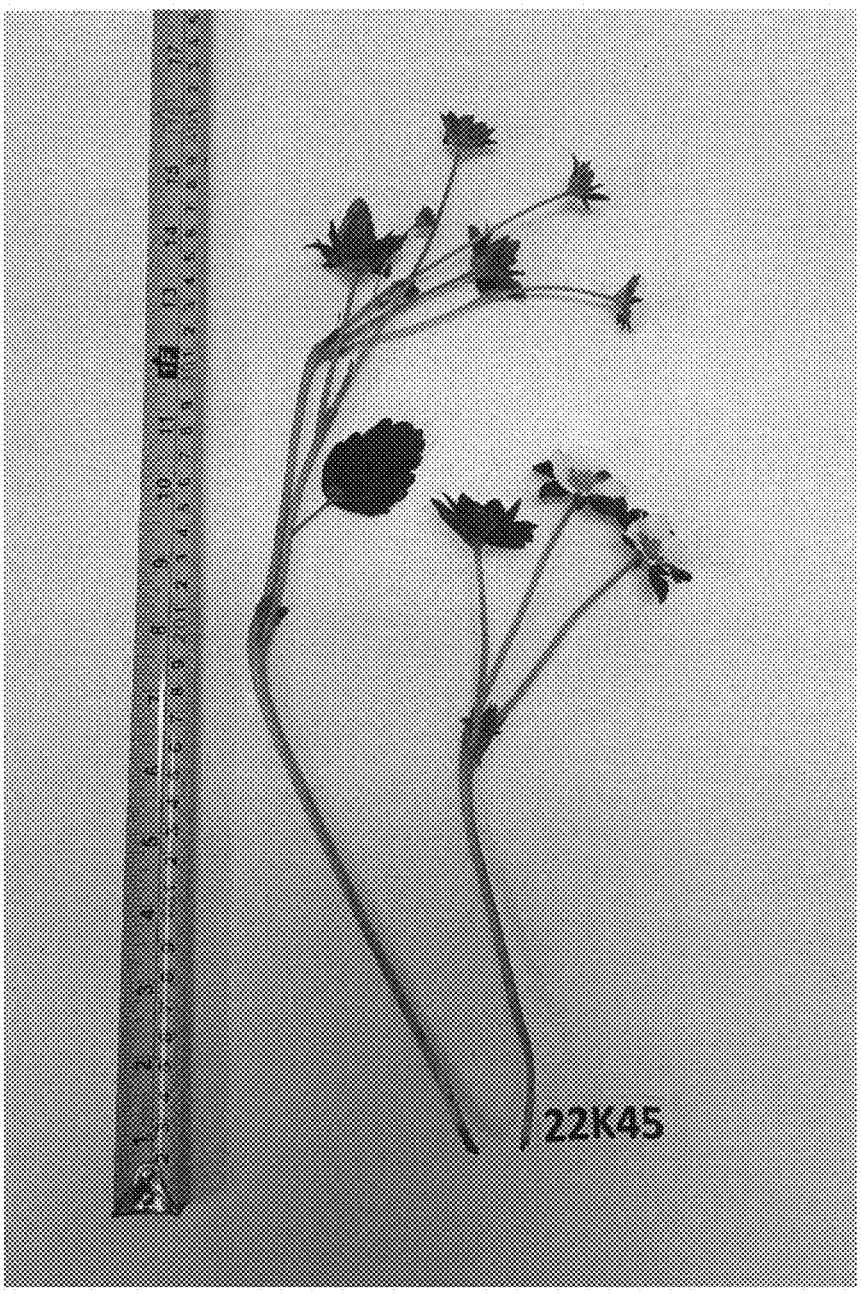
FIG. 3 shows typical inflorescences.
Figure 4:
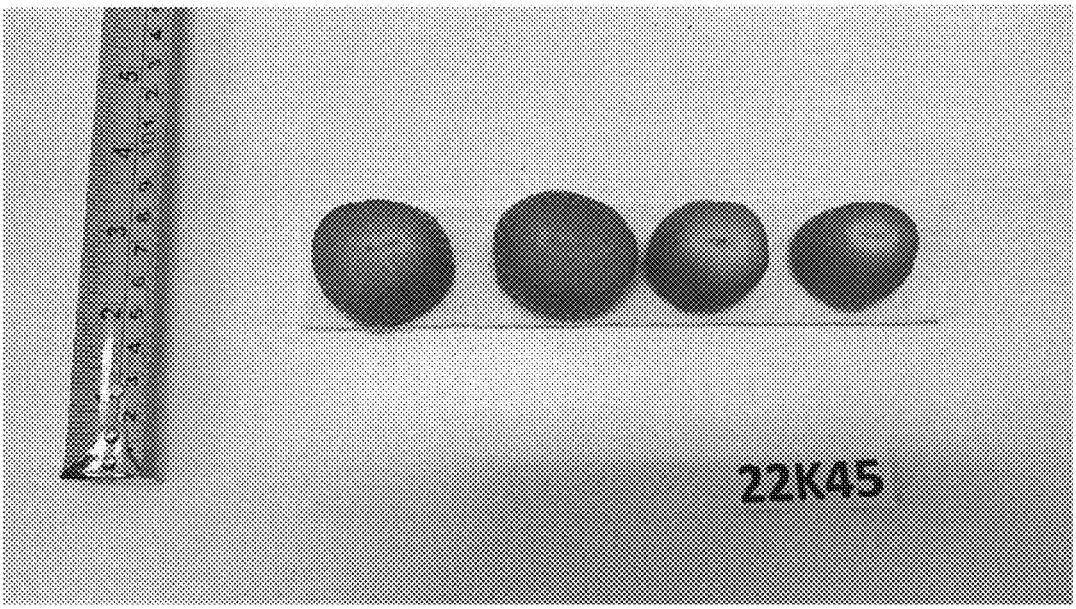
FIG. 4 shows a transverse cross-section of typical fruit, internal color and core size.
Figure 5:
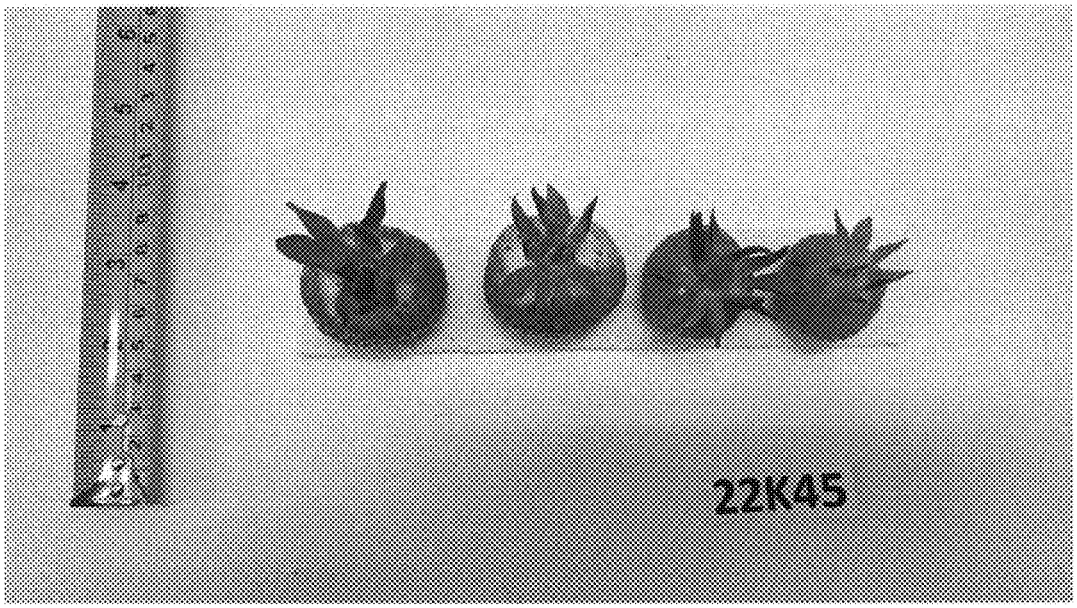
FIG. 5 shows the calyx shape and position in relation to the fruit in late-season; and, FIG. 6 shows typical plants in late-season in the fruiting field.
Figure 6:
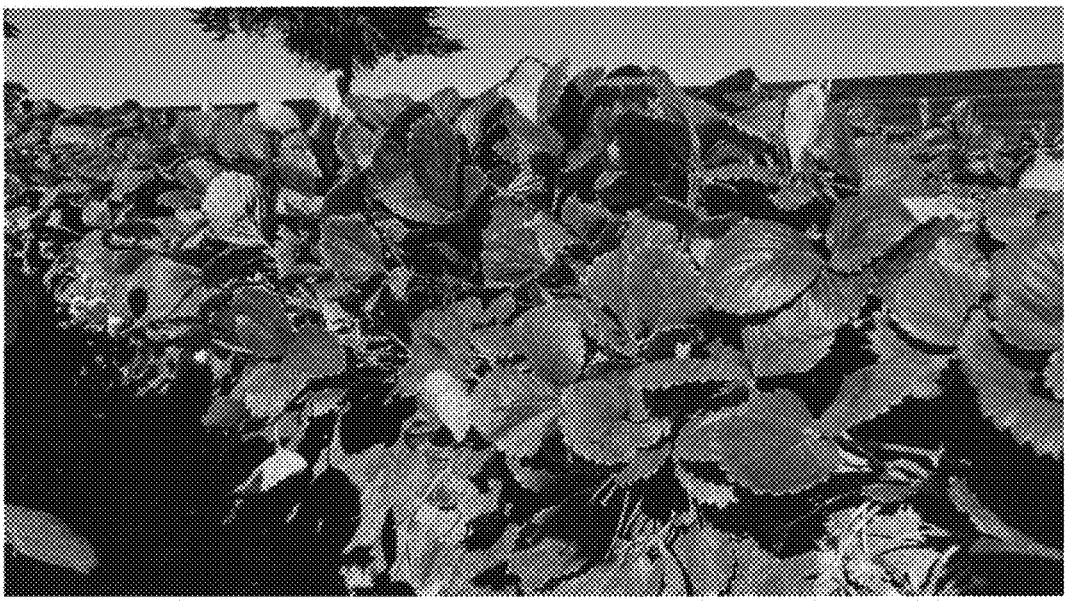

'Emilia' is a new and distinct variety of strawberry (*Fragaria* x *ananassa*). It is the result of a cross between its female parent, '1D12,' and unreleased proprietary variety, and 'Sweet Ann,' it's male parent. The female parent '1D12,' is a short-day plant, and the male parent 'Sweet Ann' is a day neutral variety. While 'Emilia' is short-day, it is partially remontant in cool coastal environments, but blooms only once in a high elevation nursery, consistent with a short-day variety. The plants of the new variety are vigorous and produce multiple crowns early after planting. 'Emilia' exhibits several characteristics which are improvements over one or both of its parent varieties, and other known cultivars. The characteristics of 'Emilia' were observed in plants in late season.

Large fruit size in strawberries has an advantage in picking, where larger fruit can be seen easier, and trays filled faster by those picking. Fruit of 'Emilia' are slightly smaller than those of an industry leading variety for fruit size, 'Sweet Ann.' This slightly smaller size is advantageous in that fruit which are too large can be difficult to fit into packaging without being damaged.

The fruit of 'Emilia,' the female parent '1D12' and the male parent 'Sweet Ann' produce mostly long conic fruit, but 'Emilia' is sometimes wedge-shaped in nature. While fruit of 'Emilia' is mostly uniform and smooth like that of 'Sweet Ann,' it can also form creases and bumps at times like that of '1D12.' The ripening pattern of 'Emilia' is more throughout the fruit, which is more attractive rather than the tip to top ripening pattern of 'Sweet Ann,' which often results in a large white shoulder. Fruit of 'Emilia' is slightly less firm than that of '1D12,' but still firm, and much firmer than fruit of 'Sweet Ann.'

The data set forth for 'Emilia' in Table 1 was collected from a plot in Moss Landing, Monterey County, Calif. in October/November in 2017. Color terminology where noted herein is in accordance with the Pantone Color Formula Guide GP 1201.

TABLE 1

Detailed Description of Characteristics of 'Emilia'

| | |
|---|---|
| SPECIFICATION: | |
| Genus/Species | *Fragaria* x *ananassa* |
| Market Name | Strawberry |
| PARENTS: | |
| Female | Proprietary variety '1D12' (Unpatented) |
| Male | 'Sweet Ann' (U.S. Plant Pat. No. 22,472). |
| PLANT: | |
| Type | Short Day. |
| Growth Habit | Semi-upright. |
| Foliage density | Dense. |
| Vigor | High. |
| Height | Average: 35.9 cm; range: 33 cm to 40 cm. |

TABLE 1-continued

| Detailed Description of Characteristics of 'Emilia' | |
|---|---|
| Width | Average: 55 cm; range: 52 cm to 58 cm. |
| Crowns | Multiple crowns produced early after planting. |
| Disease tolerance | Test plots from Cal Poly showed moderate tolerance to *Macrophomina phaseolina* (Crown rot) and a moderate tolerance to *Verticillium dahliae*. |
| LEAF: | |
| Width | Average: 166 mm; range: 130 mm to 220 mm. |
| Color | Adaxial surface: green 350 C. Abaxial surface: green 371 U. |
| Pubescence | Medium density. |
| Inter-vein blistering | Low. |
| Glossiness | Medium. |
| Variegation | None. |
| TERMINAL LEAFLET: | |
| Length | Average: 98.4 mm; range: 80 mm to 136 mm. |
| Width | Average: 83.4 mm; range: 67 mm to 99 mm. |
| Ratio length to width | 1.18. |
| Margins | Serrate to crenate. |
| Leaf shape | Orbicular. |
| Base shape | Acute. |
| Cross-section shape | Mostly concave. |
| PETIOLE: | |
| Pubescence | Medium density; direction: perpendicular. |
| Petiole color | Green 381 U. |
| Petiole length | Average: 29 cm; Range: 24.5 cm to 32 cm. |
| Petiole diameter | Average: 3.65 mm; Range: 3.12 mm to 4.34 mm. |
| STIPULE: | |
| Anthocyanin coloration | Present, mild. |
| Length | Average: 32.7 mm; Range: 25 mm to 45 mm. |
| Width | Average: 9.8 mm; Range: 8 mm to 12 mm. |
| STOLON: | |
| Anthocyanin coloration | Absent. |
| Pubescence | Low to medium; perpendicular direction. |
| Diameter | Average: 3.48 mm; Range: 3.06 mm to 4.27 mm. |
| INFLORESCENCE: | |
| Flowering time | Moderately early. |
| Position | Slightly below the canopy, but visible. |
| Number of blooms | Average: 5; Range: 3 to 8. |
| Length | Average: 30.4 cm; Range: 23 cm to 40 cm. |
| Flower | Average diameter: 27.7 mm; Range: 23 mm to 30 mm. |
| Petal arrangement | Not touching to overlapping. |
| Petal number | Average: 5.1; Range: 5 to 6. |
| Petal length | Average: 12.6 mm; Range: 10 mm to 15 mm. |
| Petal width | Average: 12.4 mm; Range: 10 mm to 15 mm. |

TABLE 1-continued

| Detailed Description of Characteristics of 'Emilia' | |
|---|---|
| Ratio length to width | 1.02. |
| Petal color | Bright white 11-0601 TPX. |
| Calyx | Slightly larger to much larger than the corolla. |
| Calyx color | Adaxial surface: green 357 C. Abaxial Surface: green 392 U. |
| Stamens | Average number: 24.9; Range: 22 to 27. |
| Pedicel | Attitude of hairs is perpendicular. |
| FRUIT | |
| Bearing | Partially remontant in cool coastal environments. |
| Shape | Well shaped, long conical, some wedge. |
| Length | Average: 58.1 mm; Range: 45 mm to 67 mm. |
| Width | Average: 41.8 mm; Range: 35 mm to 50 mm. |
| Size | Seasonal average: 29 g. |
| Achenes | Approximately level with the fruit surface. |
| Glossiness | Strong. |
| External color | Red 179 C. |
| Internal color | Flesh (excluding core): Red 1655 U. |
| Evenness of external color | Nearly or to the top of the berry when fully ripe. |
| Width of band at top devoid of achenes | Small. |
| Fruit center | Some hollowness. |
| Yield | Average grams per plant: 1626 g. |
| Firmness | Firm, firmer than parent and cultivar 'Sweet Ann.' |
| % Brix | Average: 10.9; Range: 7.6-14.0. |

The comparison statistics set forth in the following tables are with respect to characteristics observed in late season of 'Emilia.' All measurements of 'Emilia' were taken in Moss Landing, Calif. in 2017. In Table 2 and 3, the characteristics of 'Emilia' are compared with the varieties 'Sweet Ann' and 'Lucia' (U.S. Plant Pat. No. 26,974) historical data. Color identifications where noted are in accordance with the Pantone Color Formula Guide.

Plants and Foliage

The vigor of 'Emilia,' while vigorous, is less than that of 'Sweet Ann.' The plant spread, however, is larger than that of the compared varieties. The shape of the base of the mid-tier leaflet is more acute, while the compared varieties tend to have a more rounded or obtuse leaf base. The architecture of the plant was upright, like those of the compared varieties, however 'Sweet Ann' is more open than that of 'Emilia.'

TABLE 2

Foliar Characteristics of 'Emilia' Compared to 'Sweet Ann' and 'Lucia'

| Foliar Characteristics | | Cultivar 'Emilia' | 'Lucia' | 'Sweet Ann' |
|---|---|---|---|---|
| Plant height (mm) | Average | 359 | 391 | 380 |
| | Range | 330-400 | 292-490 | 290-480 |
| Plant spread (mm) | Average | 550 | 472 | 420 |
| | Range | 520-580 | 430-550 | 330-510 |

TABLE 2-continued

Foliar Characteristics of 'Emilia' Compared to 'Sweet Ann' and 'Lucia'

| Foliar Characteristics | | Cultivar 'Emilia' | 'Lucia' | 'Sweet Ann' |
|---|---|---|---|---|
| Leaf width (mm) | Average | 166 | 195 | 165 |
| | Range | 130-220 | 165-220 | 130-195 |
| Mid-tier leaflet length (mm) | Average | 98.4 | 103 | 88 |
| | Range | 80-136 | 82-116 | 72-105 |
| Mid-tier leaflet width (mm) | Average | 83.4 | 91 | 67 |
| | Range | 67-99 | 73-102 | 52-88 |
| Petiole length (mm) | Average | 290 | 268 | 220 |
| | Range | 245-320 | 230-335 | 150-280 |
| Petiole diameter (mm) | Average | 3.65 | 4.48 | 3.74 |
| | Range | 3.12-4.34 | 3.70-5.80 | 3.01-4.29 |
| Number of leaflets per leaf | | 3 | 3 | 3 |
| Leaf convexity | | Mostly concave | Slight concave | Slight concave |
| Shape of leaflet base | | Acute | Rounded to obtuse | Obtuse |
| Leaf pubescence | | Medium | Medium | Medium |
| Petiole pubescence | | Medium | Medium | Medium |
| Direction | | Perpendicular | Perpendicular | Perpendicular |
| Stipule length (mm) | Average | 32.7 | 35.7 | Not available |
| | Range | 25-45 | 30-40 | |
| Stipule anthocyanin coloration | | Yes-mild | Yes | Yes-weak |
| Leaf margins | | Serrate to crenate | Serrate to crenate | Commonly crenate |
| Leaf color adaxial surface | | 350 C | 364 U | 364 U |
| Leaf color abaxial surface | | 371 U | 363 U | 370 U |
| Petiole color | | 381 U | 366 U | 383 U |
| Leaf surface blistering | | Low | Medium | Very weak |
| Leaf surface glossiness | | Medium | High | Medium |

Flowers and Fruit

'Emilia' is a short-day variety as it blooms only once in high-elevation nurseries. It is, however, partially remontant in cool, coastal environments where it will continue to flower. Flowers of 'Emilia' had slightly more number of average petals than 'Lucia,' but less than 'Sweet Ann.' Petal size, however, was bigger in 'Emilia' than that of the compared varieties. While still visible through the canopy, the inflorescence height was smaller on 'Emilia' than in either 'Lucia' or 'Sweet Ann.' The external and internal color of 'Emilia' was slightly darker than that of 'Lucia,' and slightly lighter than that of 'Sweet Ann.' Of the many excellent fresh market qualities of 'Emilia,' its size and firmness are most notable, larger and firmer than 'Lucia,' and slightly smaller, but firmer than 'Sweet Ann.'

In Table 3, comparative data for flower and fruit characteristics for 'Emilia,' 'Lucia,' and 'Sweet Ann' are set forth.

TABLE 3

Flower and Fruit Characteristics of 'Emilia' Compared to 'Lucia' and 'Sweet Ann'

| Characteristic | | Cultivar 'Emilia' | 'Lucia' | 'Sweet Ann' |
|---|---|---|---|---|
| Petal number | Average | 5.1 | 5 | 5.4 |
| | Range | 5-6 | 5 | 5-6 |

TABLE 3-continued

Flower and Fruit Characteristics of 'Emilia' Compared to 'Lucia' and 'Sweet Ann'

| Characteristic | | Cultivar 'Emilia' | 'Lucia' | 'Sweet Ann' |
|---|---|---|---|---|
| Petal length (mm) | Average | 12.6 | 12.44 | 11.21 |
| | Range | 10-15 | 10.6-14.3 | 9.2-13 |
| Petal width (mm) | Average | 12.4 | 11.86 | 11.1 |
| | Range | 10-15 | 10-13 | 9-13 |
| Position of flower (relative to canopy) | | Slightly below, but visible | mostly exposed | most exposed, some even |
| Pedicel length (mm) | Average | 304 | 430 | 330 |
| | Range | 230-400 | 380-540 | 240-420 |
| Sepal color | Adaxial | 357 C | 364 U | 364 U |
| | Abaxial | 392 U | 3/1 U | 370 U |
| Corolla diameter (mm) | Average | 27.7 | 28.2 | 30.3 |
| | Range | 23-30 | 23.5-34 | 27-33 |
| Fruit color | External | 179 C | 1788 C | 185 C |
| | Internal | 1655 U | 179 C | 1788 C |

Leaf samples from 'Emilia,' along with three other patented selections from the breeding program including 'Lucia,' 'Scarlet,' (U.S. Plant Pat. No. 27,034) and 'Ruby June' (U.S. Plant Pat. No. 27,190) were submitted to a lab for allelic fingerprint comparison to over two hundred other varieties of strawberry in its data base. The allelic fingerprint analysis establishes that 'Emilia' is distinct and unique compared to the lab's large database of allelic fingerprints. Table 4 sets forth test results of three markers which differentiate 'Emilia.'

TABLE 4

Allelic Fingerprint Analysis

| Cultivar | Marker 1 | Marker 2 | Marker 3 |
|---|---|---|---|
| 'Emilia' | 204, 206, 214, 229 | 190, 232 | 121, 124, 130 |
| 'Lucia' | 202, 204, 206, 229 | 188, 216, 232 | 121, 124, 130, 136 |
| 'Scarlet' | 204, 206, 214, 229 | 173, 190, 232 | 121, 130 |
| 'Ruby June' | 206, 224, 229 | 188, 190, 216, 232 | 121, 130 |

Performance

Performance with respect to fruit size, yield and appearance for 'Emilia' was assessed by making comparisons with several other varieties in the breeding program, including 'Sweet Ann,' 'Lucia,' 'Ruby June,' and 'Scarlet.' All the plants for this trial were initially grown at a high elevation nursery in Macdoel, Siskiyou County, Calif. Plants of 'Emilia' and the comparison varieties were then planted and evaluated in a test plot in Moss Landing, Monterey County, Calif. in the end of 2016, through 2017.

Of the varieties tested, 'Emilia' had the second highest average seasonal yield (1,626 grams/plant), where it was only outperformed by the day-neutral variety 'Sweet Ann' with and average seasonal yield of 2,003 grams/plant. 'Emilia' also had the second largest average berry weight (29 g) of the varieties, also second only to the 31-gram average berry weight of 'Sweet Ann.'

The fruit of 'Emilia' was also rated based upon commercial appeal on a scale of 1 (worst) to 5 (best) along with several other varieties. 'Emilia' ranked in the middle with 'Ruby June' with a ranking average score of 3.75, ahead of 'Scarlet' (3.5) and behind 'Sweet Ann' (4.0) and 'Lucia' (4.5).

Table 5 shows the fruit performance of 'Emilia' as compared to 'Sweet Ann,' 'Lucia,' 'Ruby June,' and 'Scarlet.'

TABLE 5

Comparison of Performance of 'Emilia' to Other Varieties

| Cultivar | Seasonal Yield grams/plant | Seasonal Average berry weight grams/berry | Appearance Score Rating 5 = Best |
|---|---|---|---|
| 'Emilia' | 1,626 | 29 | 3.75 |
| 'Sweet Ann' | 2,003 | 31 | 4.0 |
| 'Ruby June' | 1,597 | 23 | 3.75 |

TABLE 5-continued

Comparison of Performance of 'Emilia' to Other Varieties

| Cultivar | Seasonal Yield grams/plant | Seasonal Average berry weight grams/berry | Appearance Score Rating 5 = Best |
|---|---|---|---|
| 'Lucia' | 1,584 | 25 | 4.5 |
| 'Scarlet' | 1,460 | 27 | 3.5 |

I claim:

1. A new and distinct strawberry plant named 'Emilia' as described and illustrated by the characterizations set forth above.

* * * * *